(12) United States Patent
Sehnert et al.

(10) Patent No.: US 12,189,027 B2
(45) Date of Patent: Jan. 7, 2025

(54) SYSTEM AND METHOD FOR ULTRASOUND IMAGING OF TISSUE THROUGH BONE

(71) Applicants: University of Rochester, Rochester, NY (US); Carestream Health, Inc., Rochester, NY (US)

(72) Inventors: William J. Sehnert, Rochester, NY (US); Zeljko Ignjatovic, Rochester, NY (US); Jovan Mitrovic, Rochester, NY (US)

(73) Assignees: UNIVERSITY OF ROCHESTER, Rochester, NY (US); CARESTREAM HEALTH, INC., Rochester, NY (US)

( * ) Notice: Subject to any disclaimer, the term of this patent is extended or adjusted under 35 U.S.C. 154(b) by 164 days.

(21) Appl. No.: 17/920,390

(22) PCT Filed: Apr. 26, 2021

(86) PCT No.: PCT/US2021/029188
§ 371 (c)(1),
(2) Date: Oct. 20, 2022

(87) PCT Pub. No.: WO2021/217141
PCT Pub. Date: Oct. 28, 2021

(65) Prior Publication Data
US 2023/0161033 A1 May 25, 2023

Related U.S. Application Data

(60) Provisional application No. 63/014,726, filed on Apr. 24, 2020.

(51) Int. Cl.
*A61B 8/00* (2006.01)
*A61B 8/08* (2006.01)
(Continued)

(52) U.S. Cl.
CPC ........ *G01S 15/8977* (2013.01); *A61B 8/0808* (2013.01); *A61B 8/0875* (2013.01);
(Continued)

(58) Field of Classification Search
CPC ....... A61B 8/54; A61B 8/4488; A61B 8/0808; A61B 8/5207; A61B 8/565
See application file for complete search history.

(56) References Cited

U.S. PATENT DOCUMENTS

2002/0049379 A1   4/2002   Adam et al.
2004/0210135 A1*  10/2004  Hynynen ............. A61B 8/0808
                                                          601/2

(Continued)

FOREIGN PATENT DOCUMENTS

WO   WO 2018/097989 A1   5/2018

*Primary Examiner* — Joel F Brutus
(74) *Attorney, Agent, or Firm* — Patent Technologies, LLC; Robert D. Gunderman, Jr.

(57) ABSTRACT

A transducer transmits into the bone a first plurality of excitation pulses at a plurality of frequencies and measures a plurality of echoes corresponding to the plurality of excitation pulses. An ultrasound machine calculates a plurality of energies each corresponding to a respective one of the plurality of echoes and identifies a lowest echo corresponding to a lowest of the plurality of energies. The ultrasound machine matches the lowest echo to a corresponding one of the first plurality of excitation pulses, the corresponding one of the first plurality of excitation pulses having a chosen frequency. The ultrasound machine generates an acoustic impulse response by deconvolving the corresponding one of the first plurality of excitation pulses with the lowest echo, and generates an updated sensing matrix by convolving the initial sensing matrix with the acoustic impulse response. Subsequent ultrasounds use the updated sensing matrix.

37 Claims, 6 Drawing Sheets

(51) Int. Cl.
*G01S 7/52* (2006.01)
*G01S 15/89* (2006.01)

(52) U.S. Cl.
CPC .......... *A61B 8/4488* (2013.01); *A61B 8/5207* (2013.01); *A61B 8/54* (2013.01); *A61B 8/565* (2013.01); *G01S 7/52077* (2013.01); *G01S 15/8952* (2013.01)

(56) References Cited

U.S. PATENT DOCUMENTS

2013/0336551 A1    12/2013   Clingman et al.
2017/0363725 A1    12/2017   Ignjatovic et al.

\* cited by examiner

SYSTEM AND METHOD FOR ULTRASOUND IMAGING OF TISSUE THROUGH BONE

CROSS-REFERENCE TO RELATED APPLICATION

This application claims priority to Provisional Application No. 63/014,726, filed Apr. 24, 2020, the entirety of which is incorporated by reference herein.

TECHNICAL FIELD

This patent application relates to ultrasound imaging, and in particular to ultrasound imaging of tissue that is shielded from the ultrasound transmitter by bone (e.g., a skull bone).

BACKGROUND

Ultrasound imaging, sometimes known as sonography, uses inaudible soundwaves to generate two-dimensional or three-dimensional images of internal tissue. Generally, ultrasound imaging involves transmitting soundwaves, or "excitation waves," into tissue, receiving reflected soundwaves or "echoes" from the tissue and generating an image based on the echoes. Soundwaves may be reflected when they encounter a change in acoustic impedance—referred to as "an acoustic impedance mismatch." An acoustic impedance mismatch may indicate, for example, the presence of a different tissue (e.g., an organ), and an ultrasound imaging system may use the magnitude of the mismatch to generate an image of the tissue. A brighter echo may indicate a greater acoustic impedance mismatch.

Advantages of ultrasound imaging in medical applications over other imaging technologies include, for example, that ultrasound imaging is non-ionizing, non-invasive and less expensive. One disadvantage of ultrasound imaging is that it may be unable to image tissue shielded by bone due to the significant acoustic impedance mismatch between the bone and the tissue. For example, ultrasound generally cannot be used to image the brain because the skull has a significantly higher acoustic impedance than the brain tissue. The acoustic impedance mismatch between the bone and soft tissue may cause ultrasound waves to reflect off of the bone and not reach the soft tissue. On the other hand, ultrasound soundwaves that are capable of penetrating bone may be harmful to the tissue due to, for example, the increased power requirements.

SUMMARY

Embodiments described herein include a method for obtaining an ultrasound image of tissue through bone. The method includes using a transducer having an initial sensing matrix to transmit into the bone a first plurality of excitation pulses at a plurality of frequencies and measure a plurality of echoes corresponding to the plurality of excitation pulses reflected from the bone. The method further includes calculating a plurality of energies each corresponding to a respective one of the plurality of echoes and identifying a lowest echo corresponding to a lowest of the plurality of energies, and matching the lowest echo to a corresponding one of the first plurality of excitation pulses, the corresponding one of the first plurality of excitation pulses having a chosen frequency. The method generates an acoustic impulse response by deconvolving the corresponding one of the first plurality of excitation pulses with the lowest echo. The method generates an updated sensing matrix by convolving the initial sensing matrix with the acoustic impulse response. The method transmits a second plurality of excitation pulses into the tissue and generates an image of the tissue based on echoes corresponding to the second plurality of excitation pulses and the updated sensing matrix.

Embodiments described herein also include a system for ultrasound imaging of tissue through bone. The system includes at least a transducer and an ultrasound machine, and may include a display. The transducer has an initial sensing matrix and is configured to transmit into the bone a first plurality of excitation pulses at a plurality of frequencies and measure a plurality of echoes corresponding to the plurality of excitation pulses reflected from the bone. The ultrasound machine is configured to calculate a plurality of energies each corresponding to a respective one of the plurality of echoes and identify a lowest echo corresponding to a lowest of the plurality of energies. The ultrasound machine is further configured to calculate a plurality of energies each corresponding to a respective one of the plurality of echoes and identify a lowest echo corresponding to a lowest of the plurality of energies, and to match the lowest echo to a corresponding one of the first plurality of excitation pulses, the corresponding one of the first plurality of excitation pulses having a chosen frequency. The ultrasound machine is further configured to generate an acoustic impulse response by deconvolving the corresponding one of the first plurality of excitation pulses with the lowest echo, and to generate an updated sensing matrix by convolving the initial sensing matrix with the acoustic impulse response. The transducer is configured to transmit a second plurality of excitation pulses into the tissue and generate an image of the tissue based on echoes corresponding to the second plurality of excitation pulses and the updated sensing matrix.

In embodiments described herein, before generating an image, the ultrasound machine estimates a column vector of reflectance coefficients by fitting the echoes corresponding to the second plurality of excitation pulses to a product of the updated sensing matrix and the column vector of reflectance coefficients, and converts the column vector of reflectance coefficients to a matrix of pixels. The estimation may involve a least squares estimation algorithm.

BRIEF DESCRIPTION OF THE DRAWINGS

For a detailed description of various examples, reference will now be made to the accompanying drawings in which.

DETAILED DESCRIPTION

Figure 1:
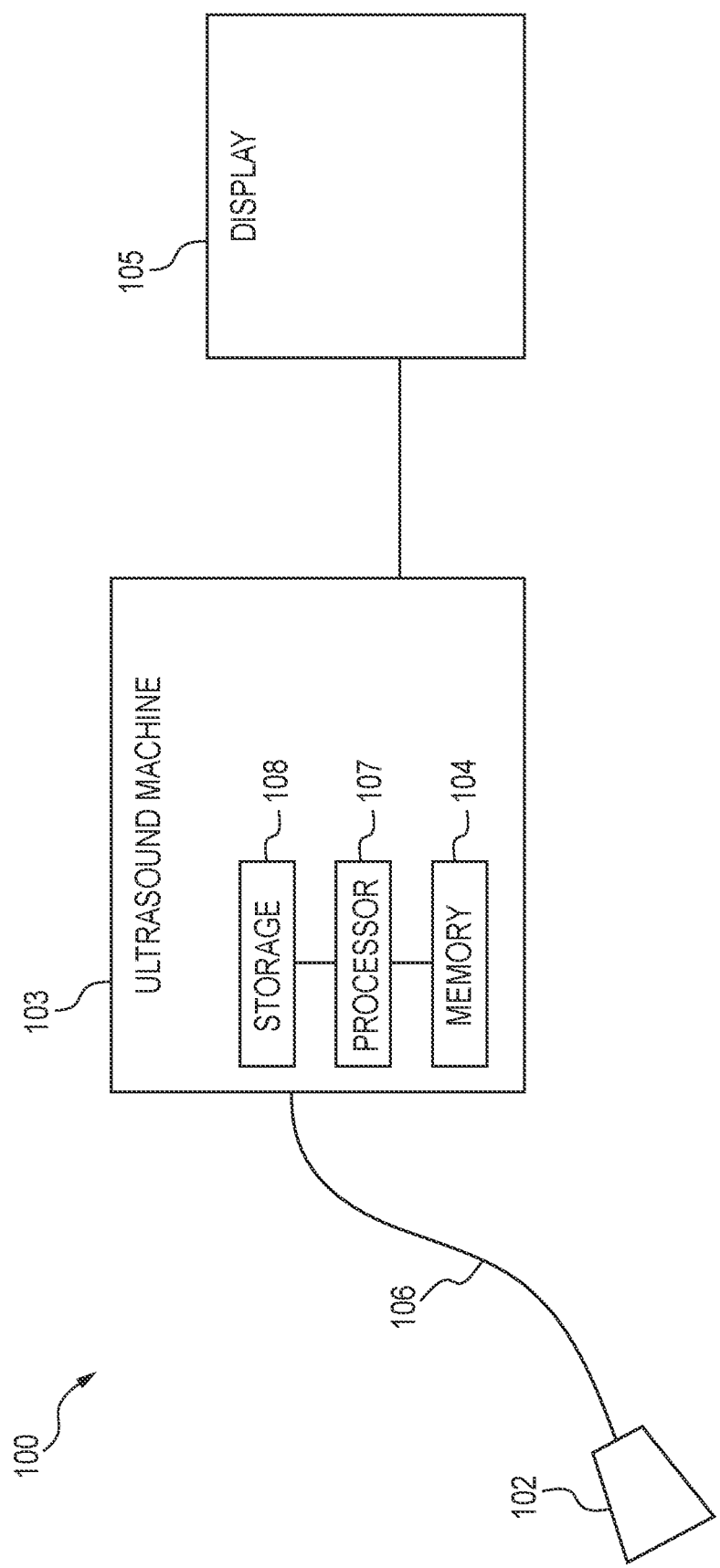
FIG. 1 shows an example ultrasound system.

A detailed description of examples of embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some of these details and even without all of the described details. Moreover, for clarity and conciseness, certain technical material that is known in the related technology has not been fully described in detail, to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Embodiments described herein relate to ultrasound imaging of tissue obstructed by bone. Due to the significant acoustic impedance mismatch between the soft tissue (e.g., brain tissue) and bone (e.g., skull layers), much of the energy transmitted by a transducer array may be reflected off the bone and never reach the target tissue due to propagation loss at higher frequencies. In addition, because the presence of bone may create multiple acoustic impedance mismatches, waves reflected from the different mismatched areas may destructively interfere, thereby reducing reflection and increasing propagation. Excitation waves having frequencies with wavelengths better matched to the bone thickness may be more likely to penetrate the bone and reach into the soft tissue. For example, an excitation wave wavelength may be better matched to the bone where the wavelength $\lambda$ is defined as:

$$\lambda = \frac{d}{n + \frac{1}{4}}$$

where d=the thickness of the bone and n is an integer.

Embodiments described herein increase the propagation of ultrasound waves through the bone to limit unwanted bone reflectance and destructive interference. Ultrasound may be used to first examine the acoustical impulse response of the bone by, for example, transmitting a short burst of plane waves at a plurality of different frequencies (e.g., from 200 kHz to 1 MHz) and receiving echoes reflected from bone layers (e.g., skull layers) for each of the plurality of excitation frequencies. The echoes may then be analyzed for received energy. Frequencies at which the received energy is minimized may be selected for use by excitation waves in subsequent imaging steps to reduce acoustic energy loses due the presence of bone layers.

Concepts discussed herein may relate to at least a portion of those described in U.S. application Ser. No. 16/414,229, filed May 16, 2019, and entitled Deep Tissue Super-Resolution Ultrasound Imaging Method and System (hereinafter the "'229 Application"), which is incorporated by reference herein in its entirety.

FIG. 1 shows a block diagram of a system 100 for ultrasound imaging according to example embodiments described herein. System 100 includes an ultrasound machine 103, which may be, for example, a special purpose medical ultrasound scanner or a general purpose computer. Ultrasound machine 103 has a processor 107 connected to memory 104. Processor 107 is configured to execute instructions necessary for ultrasound machine 103 to perform the steps described herein. Ultrasound machine 103 further includes storage 108, which may be internal or external to ultrasound machine 103 and may be used to store, for example, generated images and echo data. System 100 includes ultrasound transducer 102, which is connected to ultrasound machine 103 by connection 106. Transducer 102 is configured to send soundwaves or excitation waves into, and receive echoes from, an object or medium (e.g., tissue). Ultrasound machine 103 is configured to control transducer 102 and to receive and process data from transducer 102 via connection 106. For example, ultrasound engine 103 may provide control signals to transducer 102 to generate and send excitation pules and may receive echo data from transducer 102 for analysis and developing an ultrasound image. Connection 106 may be, for example, a wired or wireless connection. Connection 106 may incorporate one or more other components arranged at least logically and/or physically between transducer 102 and ultrasound machine 103.

System 100 also includes a display 105 configured to display ultrasound images and/or data received from ultrasound machine 103. Display 105 may be incorporated into ultrasound machine 103 or may be physically separate from ultrasound machine 103. Display 105 may have a wired or wireless connection to ultrasound machine 103. In addition, at least some of the components of ultrasound machine 103 may be incorporated into transducer 102. For example, transducer 102 may include a processor 107 and memory 104, and may perform the processing functions otherwise performed by the ultrasound machine 103. Transducer 102 may, for example, provide images to ultrasound machine 103 via a wired or wireless connection, to a display incorporated into the transducer 102, to a display connected to transducer 102 (e.g., via the internet) and/or to a server or the cloud for retrieval and viewing on any display.

Figure 2:
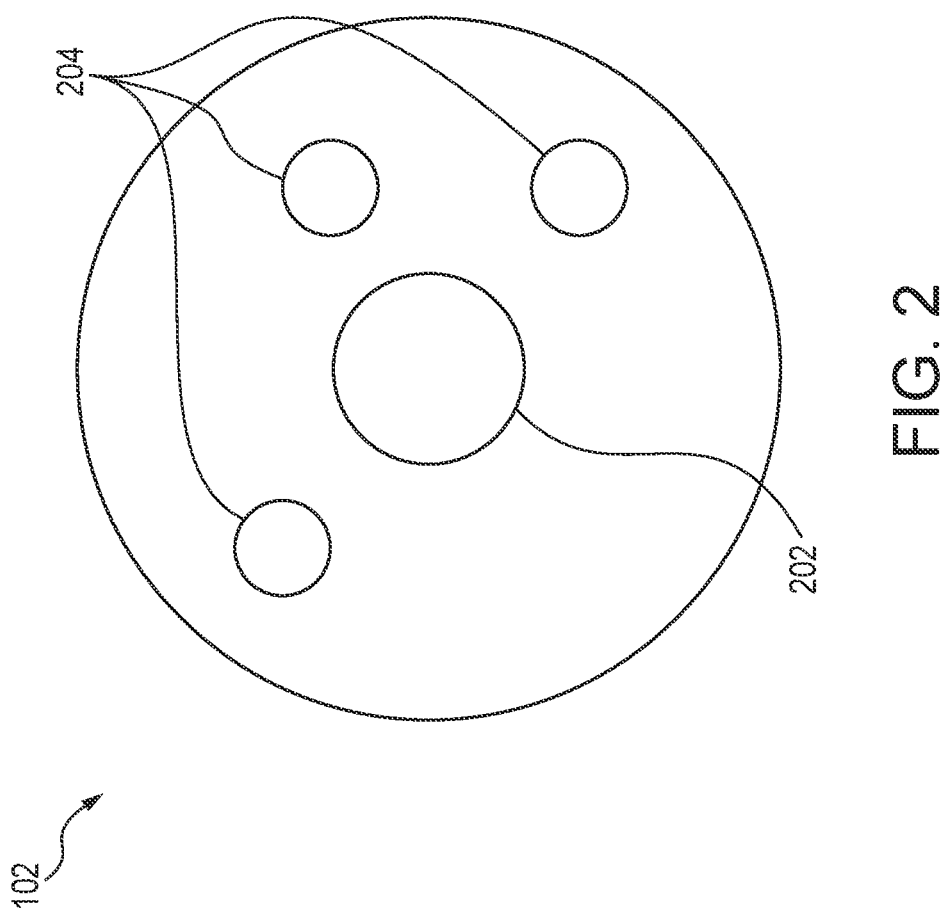
FIG. 2 shows an example arrangement of transducer elements.

FIG. 2 shows an example arrangement of transducer elements in a transducer 102 as viewed from the tissue-contacting side of the transducer 102. In this example, transducer 102 has one transmitting element 202 and three receiving elements 204. The three receiving elements 204 are arranged asymmetrically in a circular array around transmitting element 202. Arranging the receiving elements 204 asymmetrically, for example as shown in FIG. 2, may reduce imaging artifacts during the image reconstruction by reducing the condition number and increasing the rank of the sensing matrix. Transducer 102 may, however, have any number of receiving elements and/or transmitting elements. In addition, receiving elements 204 can be arranged other than in a circular array, for example in one or more linear arrays, in one or more curved arrays, or in a 2D pattern. The array may be periodic or non-periodic.

Figure 3:
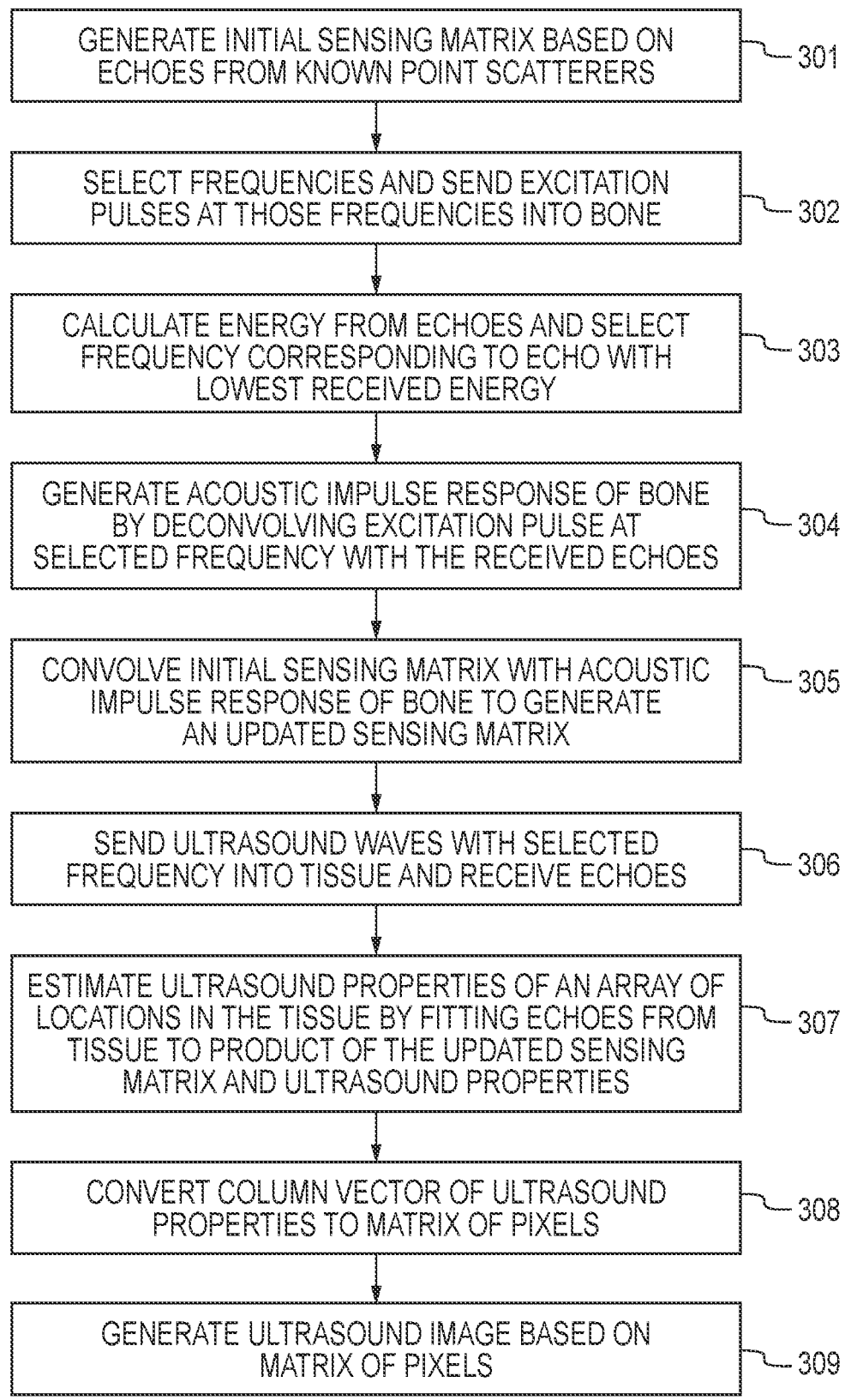
FIG. 3 shows an example ultrasound imaging method according to embodiments described herein.

FIG. 3 shows an example method of ultrasound imaging performed by system 100 (FIG. 1) to image tissue through bone. The method of FIG. 3 may be carried out entirely by transducer 102, entirely by ultrasound machine 103 or by a combination of the transducer 102, ultrasound machine 103 and/or any other computer or computers (e.g., one or more server and/or cloud computer). In addition, any step in FIG. 3 may be carried out entirely by transducer 102, entirely by ultrasound machine 103 or by a combination of the transducer 102, ultrasound machine 103 and/or any other computer or computers (e.g., one or more server and/or cloud computer).

At step 301, ultrasound machine 103 generates an initial sensing matrix based on known point scatterers in a medium. Step 301 may be performed before the ultrasound imaging, for example during manufacturing. Step 301 may also be performed, for example, during the ultrasound imaging process. Once generated, the ultrasound machine may store the sensing matrix, for example, in storage 108. If step 301 is performed before ultrasound imaging, step 301 need not be repeated during the ultrasound imaging process.

Figure 4:
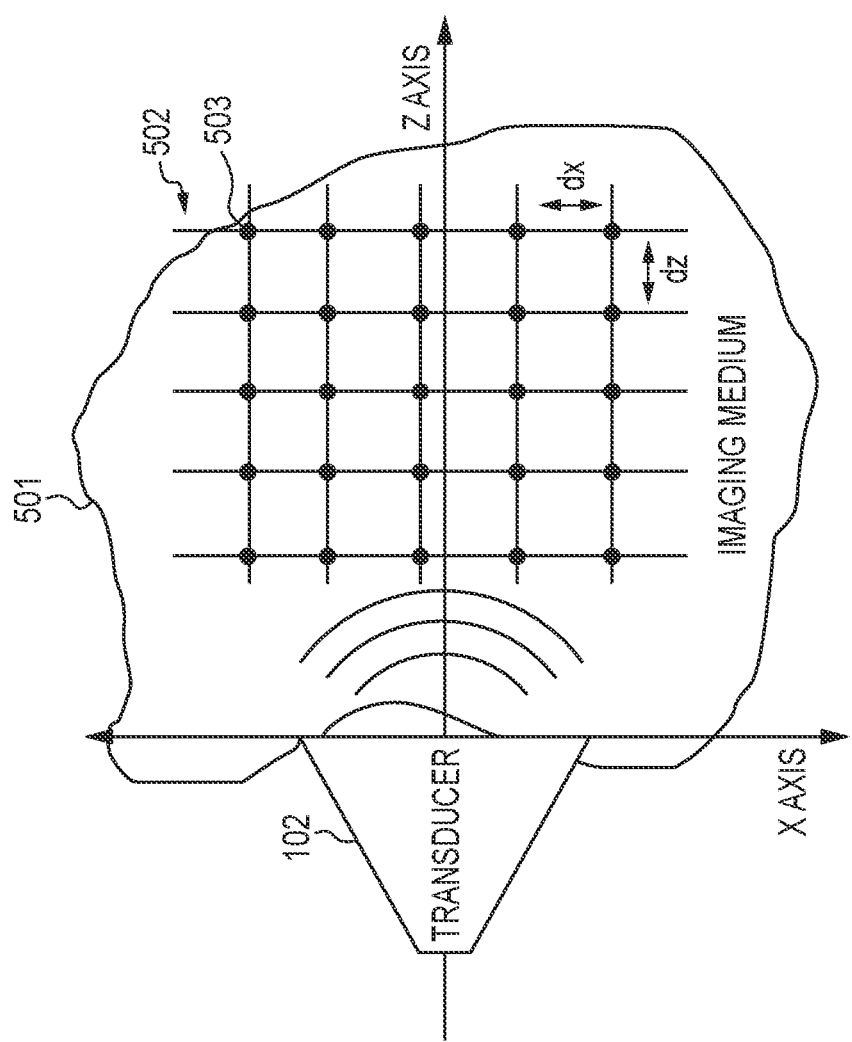
FIG. 4 shows an illustrative grid of points in a known medium.

FIG. 4 shows an example arrangement of point scatterer locations 503 upon which the initial sensing matrix may be based. The locations 503 are arranged in a grid 502 within medium 501. Grid 502 can be any shape. For example, grid 502 may be square, rectangular, triangular. Grid 502 may be periodic or non-periodic, and can be defined in, for example, rectangular coordinates or polar coordinates.

A scatterer of known reflectivity is placed at each location 503 in medium 501. The known scatterers may be, for example, high-density point scatterers. The medium 501 may be, for example, water or fat. In the example shown in FIG. 4, transducer 102 may be configured to send ultrasound waves into medium 501 for imaging in the x-z plane where the axis of propagation is in the z direction. The points 503 may be spaced from each other in an x direction by distance dx and in a z direction by distance dz. Distances dx and dz may be the same or different. In addition, dx and dz need not be constant across the grid 502. For example, a dx between two points may be different than dx between two other points.

Figure 5:
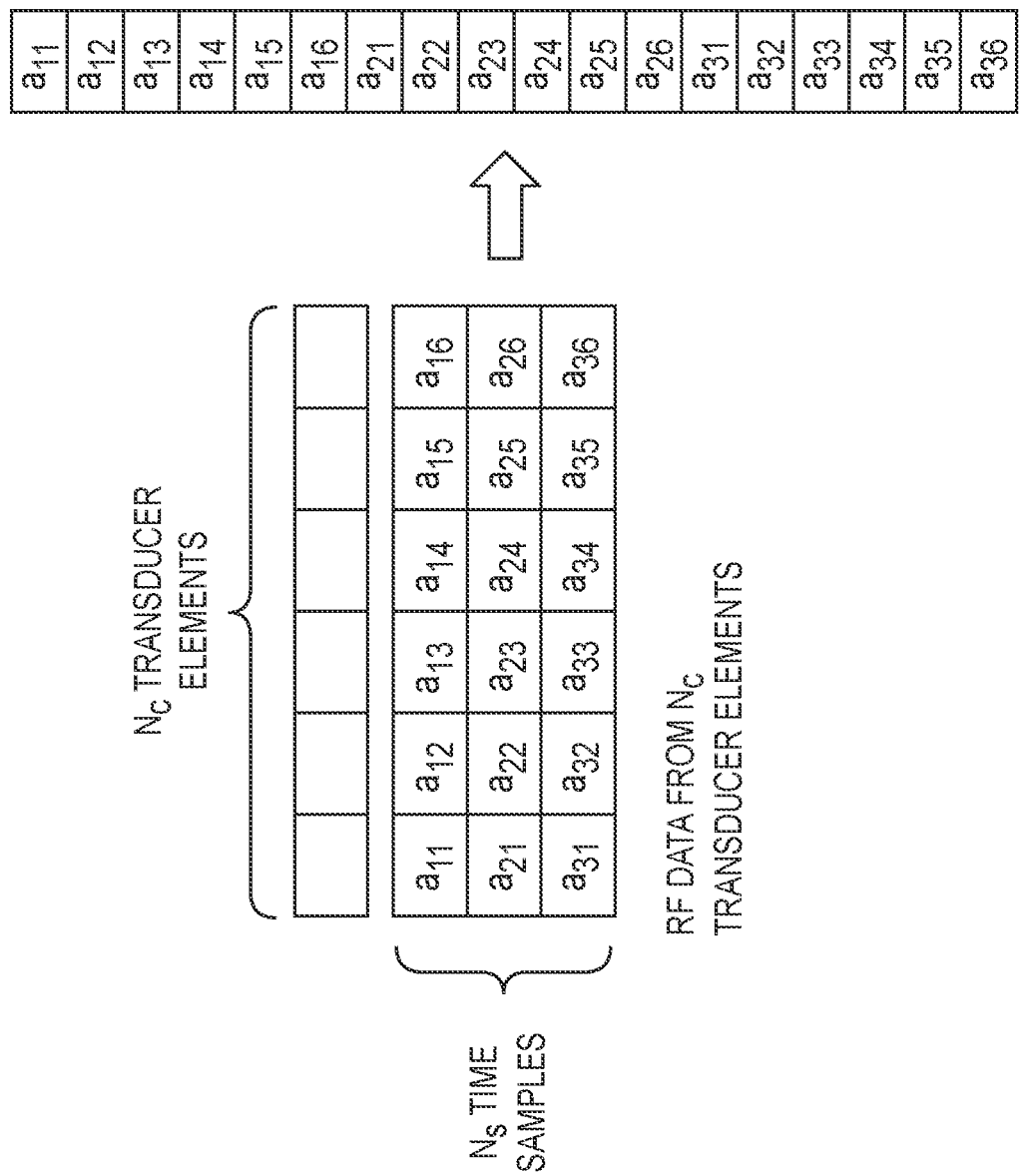
FIG. 5 illustrates forming an example sensing matrix.

The sensing matrix may be, for example, a set of column vectors that each correspond to echoes received by the transducer 102 from excitation pulses sent when only one point scatterer with maximum reflectivity is present in the medium. In this regard, a sensing matrix A may be defined as an array of the vectors $\tilde{A}_{ij}$:

$$A = [\tilde{A}^1 \tilde{A}^2 \ldots \tilde{A}^{N_x N_z}]_{N_C N_S \times N_x N_z}$$

where $N_C$ is the number of receiving elements 202 in the transducer 102, $N_S$ is the number of samples taken by each receiving element 202 per acquisition. The dimensions of sensing matrix A are $N_C N_S$ by $N_x N_z$. Each column vector $\tilde{A}_{ij}$, may correspond to echoes received by $N_C$ receiving elements 202 from the known point scatterer at a point 503 in the grid 502 at the location $(x_i, z_j)$. For example, a column vector $\tilde{A}_{N_C N_S \times 1}^{1}$ corresponds to the echoes received by the transducer 102 from a point scatterer located at point (1,1) on the grid 502 of size $N_x \times N_z$. FIG. 5 shows an example of the formation of one column vector of sensing matrix A in this regard.

The echoes used to generate vector $\tilde{A}_{ij}$ may be experimentally determined, as described above, or may be calculated. For example, the sensing matrix might be generated through simulations. Such simulations may involve, for example, using models describing the propagation, reflection and scattering of ultrasound waves in a medium and/or models describing transducer's physical properties to calculate echoes. The sensing matrix may alternatively be generated in any other manner.

In step 302, transducer 102 selects a range of frequencies and sends a plurality of excitation pulses at the range of frequencies to be reflected off the bone. The range of excitation frequencies is selected based on the physical properties of the bone, such as thickness of the bone and its relationship to the wavelength of the excitation frequency and propagation losses within the bone. As described above, the wavelength λ may be defined to have the following relationship with the bone thickness d:

$$\lambda = \frac{d}{n + \frac{1}{4}}$$

where n is an integer. For example, assuming that the average thickness of the human skull is about 6 mm, to increase energy transfer through skull layers, the wavelength λ of the selected excitation frequency may have the following relationship with the thickness:

$$\lambda = \frac{6}{n + \frac{1}{4}}$$

A range of values for integer n may be used to obtain the range of frequencies. The range of excitation frequencies may be, for example, 200 kHz to 1 MHz. The excitation waves may be, for example, a short burst of plane waves. The transducer 102 receives the reflected echoes of the excitation waves and may provide data or signals corresponding to the echoes to the ultrasound machine 103.

In step 303, the ultrasound machine 103 calculates energy from the echoes received in step 302 and selects the excitation frequency corresponding to the echo with minimum received energy. Due to the preservation of wave energy, selecting an excitation frequency that reduces energy in echoes received from the bone layers (e.g., skull layers) may increase energy transfer through the bone layers (e.g., skull layers). Each excitation pulse may result in multiple received echoes, and the calculated energy may be, for example, the variance in the energy of the received echoes for each excitation pulse. The frequency that is selected in step 303 may be the frequency corresponding to the echo with the lowest variance.

In step 304, the ultrasound machine 103 deconvolves the echo signal with the frequency selected in step 303 and the transmitted ultrasound signal corresponding to the frequency selected in step 303 to produce an acoustic impulse response of the bone. Such a deconvolution may be performed, for example, by using the following equation:

$$S(j\omega) = \frac{R(j\omega)}{P(j\omega) + \delta}$$

where S(jω) is the Fourier transform of the acoustical impulse response, R(jω) and P(jω) are the Fourier transforms of the received echo r(t) and the excitation pulse p(t), respectively, and δ is a regularization parameter. The acoustical impulse response s(t) of the bone layers may then be calculated by applying an inverse Fourier transform on S(jω).

Figure 6C:
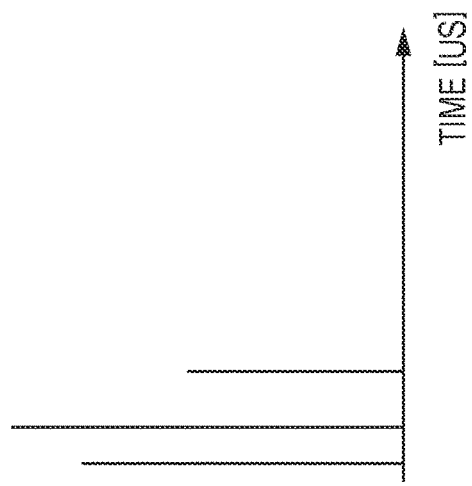
FIGS. 6a, 6b and 6c illustrate example pulses and a deconvolution according to embodiments described herein.
Figure 6B:
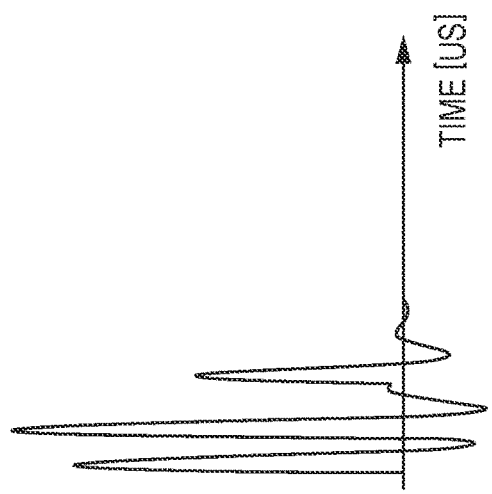
Figure 6A:
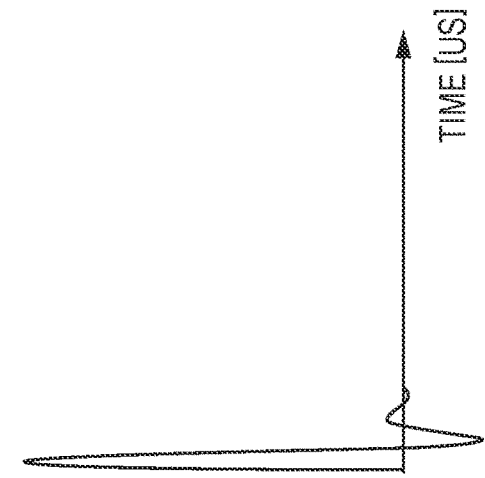

The presence of boundaries between the bone layers themselves and/or between the bone layers and surrounding soft tissue may generate reverberations. For example, if a transmitted pulse wave is a broadband one-cycle signal (as shown in FIG. 6a), after passing through the tissue boundaries of the bone layers the signal may be delayed and replicated into a plurality of one-cycle pulses (as shown in FIG. 6b) effectively reducing the bandwidth of the excitation pulse. This reverberation may cause a single scatterer behind the bone layers to be perceived as a plurality of equally spaced "ghost" scatterers. These ghost scatterers may interfere with each other resulting in a loss of contrast, resolution, and overall image quality. Inverse filtering such as deconvolution may be used to reduce the reverberation effects caused by bone layers and reduce the appearance and effects of "ghost" scatterers. An exemplary deconvolution is shown in FIG. 6c.

In step 305, ultrasound machine 103 convolves the column vectors $\tilde{A}_{ij}$ in the initial sensing matrix A from step 301 with the acoustical impulse response s(t) calculated in step 304 to generate an updated sensing matrix B. In effect, the updated sensing matrix B now combines the grid 502 of known scatterers with the effects of the bone in front of the tissue.

In step 306, the system 100 generates excitation pulses having the frequency selected in step 303, sends those excitation pulses into the tissue and receives echoes from the tissue.

In another example embodiment, the system 100 may generate an excitation pulse(s) p(t) which is a time-reversed and delayed replica of the acoustic impulse response of the bone (e.g., skull layers) s(t) as shown below:

$$p(t)=s(t_0-t)$$

where $t_0$ is chosen sufficiently large to maintain causality of excitation pulse p(t)). Choosing the excitation pulse in this manner may maximize the bandwidth of the echoes received in step 306, which may improve imaging resolution. Choosing the excitation pulse in this manner also may effectively choose the shape of the excitation pulse, as well as the frequency of the excitation pulse.

In step 307, the ultrasound machine 103 estimates ultrasound properties of an array of locations in the tissue by fitting the echoes received from the tissue to a product of the updated sensing matrix B and the ultrasound properties. The ultrasound properties may be, for example, reflectance coefficients. The received echoes from locations 503 within the tissue to be imaged (e.g., brain tissue) will be a linear combination of the vectors in the imaging matrix B. From here the imaging model can be formulated as shown below, $$Y_{N_CN_S\times 1}=B_{N_CN_S\times N_xN_z}X_{N_xN_z\times 1}+E_{N_CN_S\times 1}$$

where E is a column vector of samples of white Gaussian noise process, Y is the measured raw RF data from the received echoes, and X is a column vector of reflectance coefficients to be estimated. Estimation may be carried out using a least squares estimation algorithm, which estimates a column vector $\hat{X}_{N_xN_z\times 1}$ that minimizes L2-norm of the error term $\varepsilon=BX-Y$.

For applications where the imaged tissue is behind bone, an additional L1-norm is used as shown below, where the weighting coefficient $\beta$ is a regularization parameter. This estimation method takes advantage of sparsity in scatterer distribution in ultrasound images and may be referred to as LASSO estimation.

$$\hat{X}_{N_xN_z\times 1} = \underset{X\in[a,b]}{\mathrm{argmin}}\left(\|BX-Y\|_2^2 + \beta\|X\|_1\right)$$

Another example for estimating reflectance coefficients $\hat{X}_{N_xN_z\times 1}$ where tissue is shielded by bone is shown below. This example uses regularization with cost function employing a linear combination of L1 and L2 norms, where the weighting coefficient $\beta$ is a regularization parameter and coefficient $\alpha$ is sparsity parameter.

$$\hat{X}_{N_xN_z\times 1} = \underset{X\in[a,b]}{\mathrm{argmin}}\left(\|BX-Y\|_2^2 + \beta(\alpha\|X\|_1 + (1-\alpha)\|X\|_2^2)\right)$$

In another example shown below, which is similar to the immediately preceding example, the cost function may include a transformed version of the column vector of reflectance coefficients X that is transformed by applying a transform matrix D. For example, transform matrix D may be a Discrete Fourier transform matrix that transforms the column vector of reflectance coefficients X into its spectral components. Transform matrix D may instead be, for example, a filter matrix representing a discrete-time, linear, and time-invariant filter (e.g., differencing filter).

$$\hat{X}_{N_xN_z\times 1} = \underset{X\in[a,b]}{\mathrm{argmin}}\left(\|BX-Y\|_2^2 + \beta(\alpha\|DX\|_1 + (1-\alpha)\|DX\|_2^2)\right)$$

In step 308, the column vector of estimated reflectance coefficients X is converted to a matrix of pixels. First, the column vector of estimated reflectance coefficients X is converted to a grid matrix with dimensions representative of grid 502. Such a conversion may be effectively a reversal of the process shown in FIG. 5. As an example, a column vector X of 9 elements may be converted to a 3×3 grid such that elements 1-3 of column vector X become elements (1,1), (1,2) and (1,3) of the grid matrix, elements 4-6 of column vector X become elements (2,1), (2,2) and (2,3) of the grid matrix and elements 7-9 of column vector X become elements (3,1), (3,2) and (3,3) of the grid matrix.

Next, if dx and dz (FIG. 4) are not equal, additional processing may be required so that each element in the grid matrix corresponds to a single pixel for displaying purposes. Such additional processing may involve interpolation and/or down sampling. For example, if dx is 2 and dz is 1, additional x values may be interpolated into the matrix. Alternatively, the z values may be down sampled. In addition, the shape of the grid 502 should be accounted for in step 308.

In step 309, the ultrasound machine 103 generates an ultrasound image based on the matrix of pixels in step 308. The image may be generated in any manner. For example, the ultrasound machine 103 may apply one or more of calculating absolute values of reflectance coefficients (e.g., envelope detection), white balancing, edge enhancement, denoising, and/or log-compression to the matrix of pixels generated in step 308 to generate the image.

Alternatively, the ultrasound machine 103 may use neural networks to generate the image. For example, ultrasound machine 103 may use a neural network architecture that converts a measured raw RF data column vector Y (e.g., an echo) directly into an image. Such a neural network architecture may be, for example, a fully-convolutional neural network. A tool such as PyTorch or Tensorflow may be used to derive the neural networks. The data to the train the neural network may be obtained, for example, through simulated models. The simulated models may be generated, for example, using a tool such as k-Wave.

Another approach would be to derive a neural network that converts a measured raw RF data column vector Y into a column vector of reflectance coefficients X, which may mimic the estimation described above. The data to train the neural networks for this approach may be obtained, for example, by using one of the estimations described above in step 307.

Once generated, the image may be displayed on display 105. Alternatively, or in addition, the image may be saved in storage 108.

In the embodiments described above in this patent specification, all of the elements of a transducer array, for example all 48 elements, can be driven to transmit imaging ultrasound energy into the patient or object being imaged, but less than all, for example, only two, can be used to receive ultrasound energy (echoes) for imaging. However, not all the transducer elements need be used to transmit. For example, if the transducers are in a linear or curved array, and there is a total of 48 transducer elements available to transmit, a few of these elements that are over or near a ridge at a suture of skull bones can be disabled so they do not transmit an ultrasound pulse that the remaining transducer elements transmit. The number of transmitting elements can still be greater than the number of elements that receive reflections of the transmitted pulse, but image artifacts can be significantly reduced by disabling or not driving the transmitting elements that are over or near a structure such a ridge.

The methods and systems described herein may be used to obtain an ultrasound image of any tissue that is behind bone. While the skull and brain are the primary example provided herein, another example that may be used with embodiments described herein is imaging the spinal cord through vertebrae. In addition, embodiments described herein may be used to take an ultrasound image of any medium that is behind another medium of substantially higher acoustic impedance and that suffers from the issues of propagation loss described herein.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

The invention claimed is:

1. A method for obtaining an ultrasound image of tissue through bone, the method comprising:
   using a transducer having an initial sensing matrix to transmit into the bone a first plurality of excitation pulses at a plurality of frequencies and measure a first plurality of echoes corresponding to the first plurality of excitation pulses reflected from the bone;
   calculating a plurality of energies each corresponding to a respective one of the first plurality of echoes and identifying a lowest echo corresponding to a lowest of the plurality of energies;
   matching the lowest echo to a corresponding one of the first plurality of excitation pulses, the corresponding one of the first plurality of excitation pulses having a chosen frequency;
   generating an acoustic impulse response by deconvolving the corresponding one of the first plurality of excitation pulses with the lowest echo;
   generating an updated sensing matrix by convolving the initial sensing matrix with the acoustic impulse response; and
   transmitting a second plurality of excitation pulses into the tissue and generating an image of the tissue based on a second plurality of echoes corresponding to the second plurality of excitation pulses and the updated sensing matrix.

2. The method of claim 1, wherein the generating an image of the tissue comprises:
   a. estimating a column vector of reflectance coefficients;
   b. converting the column vector of reflectance coefficients to a matrix of pixels; and
   c. generating the image based on the matrix of pixels.

3. The method of claim 2, wherein the estimating the column vector of reflectance coefficients comprises using:

$$\hat{X}_{N_x N_z \times 1} = \underset{X \in [a,b]}{\operatorname{argmin}}(\|BX - Y\|_2^2 + \beta \|X\|_1)$$

where $\hat{X}_{N_x N_z \times 1}$ is the column vector of reflectance coefficients, Y is measured raw RF data from the received echoes corresponding to the second plurality of excitation pulses, B is the updated sensing matrix and $\beta$ is a weighting coefficient used as a regularization parameter.

4. The method of claim 2, wherein the estimating the column vector of reflectance coefficients comprises using:

$$\hat{X}_{N_x N_z \times 1} = \underset{X \in [a,b]}{\operatorname{argmin}}(\|BX - Y\|_2^2 + \beta(\alpha \|X\|_1 + (1-\alpha)\|X\|_2^2))$$

where $\hat{X}_{N_x N_z \times 1}$ is the column vector of reflectance coefficients, Y is measured raw RF data from the received second plurality of echoes corresponding to the second plurality of excitation pulses, B is the updated sensing matrix, $\beta$ is a weighting coefficient used as a regularization parameter and $\alpha$ is sparsity parameter.

5. The method of claim 2, wherein the estimating the column vector of reflectance coefficients comprises using:

$$\hat{X}_{N_x N_z \times 1} = \underset{X \in [a,b]}{\operatorname{argmin}}(\|BX - Y\|_2^2 + \beta(\alpha \|DX\|_1 + (1-\alpha)\|DX\|_2^2))$$

where $\hat{X}_{N_x N_z \times 1}$ is the column vector of reflectance coefficients, Y is measured raw RF data from the received echoes corresponding to the second plurality of excitation pulses, B is the updated sensing matrix, $\beta$ is a weighting coefficient used as a regularization parameter, $\alpha$ is sparsity parameter and D is a transform matrix.

6. The method of claim 5, wherein the transform matrix D is a discrete Fourier transform.

7. The method of claim 5, wherein the transform matrix D is a filter matrix representing a discrete-time, linear, and time-invariant filter.

8. The method of claim 1, further comprising determining the plurality of frequencies based on the relationship of a corresponding plurality of wavelengths to a thickness of the bone.

9. The method of claim 8, wherein the plurality of wavelengths $\lambda$ are determined for a plurality of integers n:

$$\lambda = \frac{d}{n + \frac{1}{4}}$$

where d is the thickness of the bone.

10. The method of claim 9, wherein each of the plurality of frequencies is in the range of 200 kHz to 1 MHz.

11. The method of claim 1, wherein the step of generating an acoustic impulse response comprises calculating the acoustic impulse response using the following equation:

$$S(j\omega) = \frac{R(j\omega)}{P(j\omega) + \delta}$$

where S(jω) is the Fourier transform of the acoustical impulse response, R(jω) and P(jω) are the Fourier transforms of the received echo r(t) and the excitation pulse p(t), respectively, and δ is a regularization parameter.

12. The method of claim 1, wherein the bone comprises skull bone and the tissue comprises brain tissue.

13. The method of claim 1, wherein the bone comprises vertebrae and the tissue comprises spinal cord tissue.

14. The method of claim 1, further comprising generating the initial sensing matrix based on known point scatterers in a known medium.

15. The method of claim 1, wherein the image is generated using neural networks.

16. The method of claim 15, wherein the neural networks are configured to convert a raw RF data vector into an image.

17. The method of claim 16, wherein the neural network is trained using data obtained through simulated models.

18. The method of claim 15, wherein the neural networks are configured to convert measured raw RF data column vector into a column vector of reflectance coefficients.

19. The method of claim 18, wherein the neural network is trained using data obtained by a LASSO estimation.

20. The method of claim 1, wherein the second plurality of excitation pulses are generated with the chosen frequency.

21. The method of claim 1, wherein the second plurality of excitation pulses are a time-reversed and delayed replica of the acoustic impulse response.

22. A system for ultrasound imaging of tissue through bone, the system comprising:
   a transducer having an initial sensing matrix and configured to transmit into the bone a first plurality of excitation pulses at a plurality of frequencies and measure a first plurality of echoes corresponding to the first plurality of excitation pulses reflected from the bone;
   an ultrasound machine configured to:
      calculate a plurality of energies each corresponding to a respective one of the first plurality of echoes and identify a lowest echo corresponding to a lowest of the plurality of energies;
      calculate a plurality of energies each corresponding to a respective one of the plurality of echoes and identify a lowest echo corresponding to a lowest of the plurality of energies;
      match the lowest echo to a corresponding one of the first plurality of excitation pulses, the corresponding one of the first plurality of excitation pulses having a chosen frequency;
      generate an acoustic impulse response by deconvolving the corresponding one of the first plurality of excitation pulses with the lowest echo; and
      generate an updated sensing matrix by convolving the initial sensing matrix with the acoustic impulse response,
   wherein the transducer is further configured to transmit a second plurality of excitation pulses into the tissue and receive a second plurality of echoes corresponding to the second plurality of excitation pulses, and
   wherein the ultrasound machine is configured to generate an image of the tissue based on the second plurality of echoes corresponding to the second plurality of excitation pulses and the updated sensing matrix.

23. The system of claim 22, wherein the ultrasound machine is configured to generate an image of the tissue by:
   d. estimating a column vector of reflectance coefficients;
   e. converting the column vector of reflectance coefficients to a matrix of pixels; and
   f. generating the image based on the matrix of pixels.

24. The system of claim 23, wherein the ultrasound machine is configured to estimate the column vector of reflectance coefficients using:

$$\hat{X}_{N_x N_z \times 1} = \underset{X \in [a,b]}{\operatorname{argmin}}(\|BX - Y\|_2^2 + \beta\|X\|_1)$$

where $\hat{X}_{N_x N_z \times 1}$ is the column vector of reflectance coefficients, Y is measured raw RF data from the received echoes corresponding to the second plurality of excitation pulses, B is the updated sensing matrix and β is a weighting coefficient used as a regularization parameter.

25. The system of claim 23, wherein the ultrasound machine is configured to estimate the column vector of reflectance coefficients using:

$$\hat{X}_{N_x N_z \times 1} = \underset{X \in [a,b]}{\operatorname{argmin}}(\|BX - Y\|_2^2 + \beta(\alpha\|X\|_1 + (1-\alpha)\|X\|_2^2))$$

where $\hat{X}_{N_x N_z \times 1}$ is the column vector of reflectance coefficients, Y is measured raw RF data from the received second plurality of echoes corresponding to the second plurality of excitation pulses, B is the updated sensing matrix, β is a weighting coefficient used as a regularization parameter and α is sparsity parameter.

26. The system of claim 23, wherein the ultrasound machine is configured to estimate the column vector of reflectance coefficients using:

$$\hat{X}_{N_x N_z \times 1} = \underset{X \in [a,b]}{\operatorname{argmin}}(\|BX - Y\|_2^2 + \beta(\alpha\|DX\|_1 + (1-\alpha)\|DX\|_2^2))$$

where $\hat{X}_{N_x N_z \times 1}$ is the column vector of reflectance coefficients, Y is measured raw RF data from the received second plurality of echoes corresponding to the second plurality of excitation pulses, B is the updated sensing matrix, β is a weighting coefficient used as a regularization parameter, α is sparsity parameter and D is a transform matrix.

27. The system of claim 22, wherein the ultrasound machine is further configured to determine the plurality of frequencies based on the relationship of a corresponding plurality of wavelengths to a thickness of the bone.

28. The system of claim 22, wherein the ultrasound machine is further configured to determine the plurality of wavelengths A for a plurality of integers n using:

$$\lambda = \frac{d}{n + \frac{1}{4}}$$

where d is the thickness of the bone.

29. The system of claim 28, wherein each of the plurality of frequencies is in the range of 200 kHz to 1 MHz.

30. The system of claim 22, wherein the ultrasound machine is further configured to generate the acoustic impulse response by calculating the acoustic impulse response using the following equation:

$$S(j\omega) = \frac{R(j\omega)}{P(j\omega) + \delta}$$

where $S(j\omega)$ is the Fourier transform of the acoustical impulse response, $R(j\omega)$ and $P(j\omega)$ are the Fourier transforms of the received echo $r(t)$ and the excitation pulse $p(t)$, respectively, and $\delta$ is a regularization parameter.

31. The system of claim 22, wherein the bone comprises skull bone and the tissue comprises brain tissue.

32. The system of claim 22, wherein the bone comprises vertebrae and the tissue comprises spinal cord tissue.

33. The system of claim 22, wherein the transducer and the ultrasound machine are integrated into a handheld unit.

34. The system of claim 22, further comprising a display configured to display the image.

35. The system of claim 34, wherein the ultrasound machine is configured to send the image to a server, and the display is configured to receive the image from a server.

36. The system of claim 22, wherein the second plurality of excitation pulses are generated with the chosen frequency.

37. The system of claim 22, wherein the second plurality of excitation pulses are a time-reversed and delayed replica of the acoustic impulse response.

* * * * *